United States Patent
Nagaoka et al.

(10) Patent No.: US 6,500,388 B1
(45) Date of Patent: Dec. 31, 2002

(54) AUTOMATICALLY ANALYZING APPARATUS

(75) Inventors: Yoshihiro Nagaoka, Ishioka (JP); Ryo Miyake, Tsukuba (JP); Masaharu Nishida, Hitachinaka (JP); Takeshi Shibuya, Hitachinaka (JP); Takao Terayama, Ushiku (JP); Hiroshi Mitsumaki, Mito (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/154,698

(22) Filed: Sep. 17, 1998

(30) Foreign Application Priority Data

Sep. 18, 1997 (JP) ............................................... 9-253010

(51) Int. Cl.⁷ .......................... G01N 35/10; B01L 11/00
(52) U.S. Cl. ........................... 422/64; 422/63; 422/100; 436/47; 436/49; 436/179; 436/180; 134/21; 134/22.11; 134/24; 134/26; 134/27; 134/169 R
(58) Field of Search ........................... 422/63, 64, 100; 141/155; 73/864.01, 864.12; 436/47, 49, 179, 180; 134/21, 22.11, 24, 26, 27, 169 R (56) References Cited

U.S. PATENT DOCUMENTS

| | | | | |
|---|---|---|---|---|
| 4,039,349 A | * | 8/1977 | Kwasnoski et al. ........... 134/10 |
| 4,094,329 A | * | 6/1978 | Evans ....................... 134/56 R |
| 4,227,886 A | * | 10/1980 | Bullock et al. ............. 23/230 R |
| 4,313,735 A | * | 2/1982 | Yamashita et al. ......... 23/230 R |
| 4,803,050 A | * | 2/1989 | Mack ........................... 422/65 |
| 5,104,808 A | * | 4/1992 | Laska et al. ................... 436/48 |
| 5,147,610 A | * | 9/1992 | Watanabe et al. ............. 422/64 |
| 5,192,505 A | * | 3/1993 | Sakagami .................... 422/64 |
| 5,876,511 A | * | 3/1999 | Till ............................ 134/22.1 |
| 5,948,358 A | * | 9/1999 | Satio .......................... 422/64 |

FOREIGN PATENT DOCUMENTS

| | | | |
|---|---|---|---|
| EP | 0 769 547 A2 | 4/1997 | |
| JP | 60-53850 | * 3/1985 | .......... G01N/35/02 |
| JP | 6-160398 | * 3/1985 | .......... G01N/35/02 |

* cited by examiner

Primary Examiner—Jill Warden
Assistant Examiner—Kathryn Bex
(74) Attorney, Agent, or Firm—Antonelli, Terry, Stout, & Kraus, LLP

(57) ABSTRACT

An automatically analyzing apparatus includes a plurality of reaction containers for reacting a sample with a reagent, and a reaction container washing unit for washing the reaction containers through a plurality of washing steps. The reaction container washing unit includes a plurality of storage parts in each of which washing liquid containing therein reacted substance is reserved. The plurality of storage parts are sorted with different reacted substance concentrations. A supply part of the reaction container washing unit selects washing liquid of a desired reacted substance concentration among the plurality of storage parts in accordance with respective washing conditions of the reaction containers and supplies the selected washing liquid into the reaction containers for washing the respective reaction containers.

4 Claims, 9 Drawing Sheets

| WASHING STEP | 1 DISCARD OF REACTED LIQUID WASHING WITH DETERGENT | 2 DISCARD OF RETERGENT LIQUID WASHING | 3 SUCTION OF WASHING LIQUID WASHING | 4 SUCTION OF WASHING LIQUID COMPLETE SUCTION | 5 DISCHARGE OF PURE WATER | 6 CELL BLANK | 7 SUCTION OF PURE WATER | 8 COMPLETE SUCTION |
|---|---|---|---|---|---|---|---|---|
| SUCKED LIQUID | REACTED LIQUID | WASHING LIQUID | WASHING LIQUID | WASHING LIQUID | — | — | CELL BLANK LIQUID | CELL BLANK LIQUID |
| CONSENTRATION INDEX | 1 | 3 | 5 | 7 | — | — | 9 | 9 |
| REUSE | DISCARD | DISCARD | REUSE | REUSE | — | — | REUSE | — |
| CONTAINER | 161 | 163 | 155 | 157 | — | — | 159 | 159 |
| DISCHARGED LIQUID | DETERGENT + REUSED LIQUID | REUSED LIQUID | REUSED LIQUID | — | PURE WATER | — | — | — |
| CONCENTRATION INDEX | 5 | 7 | 9 | — | PURE WATER | — | — | — |
| CONTAINER | 142+155 | 157 | 159 | — | 148 | — | — | — |

FIG. 5

CELL BLANK LIQUID

FIG. 6

WASHING STEP AND VARIATION IN CONCENTRATION

FIG. 7

COMPARISON BETWEEN THEORETICAL CALCULATION AND RESULT OF EXPERIMENTS

AUTOMATICALLY ANALYZING APPARATUS

BACKGROUND OF THE PRESENT INVENTION

The present invention relates to an automatically analyzing apparatus for quantifying a concentration of a substance solved in liquid, and in particular, to an automatically analyzing apparatus for analyzing components of biological fluid or water.

There have well-known many automatically analyzing apparatus. For example, Japanese Laid-Open Patent Publication No. H6-160398 discloses an automatically analyzing apparatus in which a sample and a reagent are reacted with each other in a reaction container so as to analyze thus obtained reacted liquid, thereafter, the reaction container is washed, and then, a next sample and the reagent are again reacted with each other in the container for next analysis. Accordingly, this apparatus includes a washing mechanism which washes several reaction containers one by one by the following steps:

Reacted liquid in a first reaction container after measurements, is sucked up by a nozzle, and is discharged into a disposal container. Then, detergent liquid is sucked up by a nozzle from a detergent container and is then discharged into the reaction container.

Next, the detergent liquid in the reaction container is sucked up, and is then discharged as waste liquid.

Then, detergent liquid is sucked up by the nozzle from the detergent container, and is then discharged into the reaction container. Thereafter, the detergent liquid is sucked up and then, is discharged as waste liquid. With the repetitions of the above-mentioned steps, and during fifth cycle, the liquid is sucked up until the reaction container is dried.

The washing device in the automatically analyzing apparatus disclosed in the above-mentioned Japanese Laid-Open Patent Publication No. H6-160398, is adapted to discharge and suck up the detergent liquid by 5 times in total. With the use of the washing process, pure water, alkaline washing agent, acid washing agent or the like is selected as detergent liquid in accordance with reacted liquid in order to enhance the efficiency.

Further, Japanese Laid-Open Patent Publication No. S60-53850 discloses a washing device for a medical microplate, in which high pressure washing liquid is jetted onto the microplate formed therein several reaction containers in a matrix-like pattern, so as to wash the several reaction containers or cells in the microplate at substantially the same time. The washing mechanism in this apparatus carries out the following steps:

Pre-washing step: High pressure washing liquid is jetted so as to wash out reacted liquid; and Disinfecting step: Antiseptic liquid is jetted in so as to disinfect the microplate.

Main washing step: High pressure washing liquid is jetted so as to wash out the antiseptic liquid.

Since high pressure washing liquid is jetted, the reacted liquid is sufficiently cleaned off from the reaction containers at the pre-washing step, and accordingly, substantially no reacted substance is solved in the antiseptic liquid in the next disinfecting step. Accordingly, the antiseptic liquid used at the disinfecting step can be repeatedly used. That is, the antiseptic liquid sucked up from an antiseptic liquid tank and used for disinfecting the microplate is returned into the antiseptic liquid tank after use, and is then used repeatedly. At the final main washing step, only wash-out of the antiseptic liquid is carried out, and at this step, substantially no reacted substance is solved in the washing liquid. Thus, the washing liquid used at the main washing step can be reused at the pre-washing step.

Further, Japanese Laid-Open Patent Publication No. H5-240866 discloses an automatically analyzing apparatus in which a cell blank after washing is measured, and the thus measured cell blank is compared with a cell blank measured during next washing so as to carry out analysis.

The purpose of the washing is to completely remove reacted substance remaining in the reacted liquid in the reaction container in order to prevent reacted liquid after completion of analysis from causing affection during next analysis.

The washing mechanism in the automatically analyzing apparatus disclosed in the Japanese Laid-Open Patent publication No. H6-160398, repeats the discharge and suction of washing liquid by four times. In this case, the quantity of reacted substance remaining in the reaction container is decreased successively each time when washing liquid is discharge and sucked up, and when the washing liquid is sucked up at the final fifth step, substantially no reacted substance remains in the reaction container, and accordingly, there is no affection in next analysis.

In other words, the quantity of reaction substance solved in the washing liquid is decreased successively each time when the washing liquid is discharged and sucked up, and the quantity of reacted substance solved in the washing liquid becomes less as the washing steps are progressed.

Meanwhile, since reacted liquid would remain by an extremely slight quantity in the reaction container after the reacted liquid is sucked up from the reaction container at the first washing step, not only washing liquid which does not contain reacted substance but also clean washing liquid which has been used at one of the posterior steps, such as fourth or fifth washing step, may be discharged to clean the reaction container by a substantial degree, and further, if pure water is used at the final fifth washing step, it is possible to expect satisfactory washing effect.

Further, a washing mechanism in an automatically analyzing apparatus disclosed in Japanese Laid-Open patent Publication No. H-616039, uses clean washing liquid containing no reacted substance at every of washing steps, and waste liquid obtained after reacted liquid and washing liquid are sucked up is discarded through one and the same flow passage. Accordingly, at the first one of washing steps, washing liquid which is cleaner than that required, is used, and at the posterior washing steps, washing liquid having a high washing capability, which does not substantially contain reacted liquid, are wastefully discarded.

Further, in the washing device for medical microplates, disclosed in Japanese Laid-Open Patent Publication No. S60-53850, washing liquid obtained after the main washing is reused in order to reduce the consumption of washing liquid. However, the washing of reacted liquid has to be completed at the pre-washing step, and accordingly, it is required to jet high pressure washing liquid, causing consumption of a huge quantity of washing liquid, and further, washing liquid used at the pre-washing step is all discarded.

Further, the Japanese Laid-Open Patent Publication No. H5-240866 discloses the measurement of a cell blank only for enhancing the accuracy of analysis, but fails to disclose the reuse of washing liquid.

SUMMARY OF THE INVENTION

An object of the present invention is to provide an automatically analyzing apparatus incorporating a washing mechanism which can reduce the consumption of washing liquid without deteriorating the washing capability, by reusing washing liquid having different concentrations of solved reacted substance, selectively, for washing steps.

The above-mentioned object can be attained by the provision, in a reaction container washing means, of a plurality of storage containers in which washing liquid having different concentration of solved reacted substance are temporarily reserved, respectively, and a washing liquid supply means for selectively supplying washing liquid from the storage containers into a part which requires washing.

Alternatively, in such a case that the reaction container washing means incorporates a reacted liquid suck-up means for sucking up reacted liquid from a reaction container and a washing liquid supply means for supplying washing liquid into a reaction container, the above-mentioned object can be attained in such a way that washing liquid used for washing at a certain washing step is used as washing liquid for a washing step which is anterior to this certain step.

Alternatively, it is solved in such a way that. washing liquid sucked up by the reacted liquid suck-up means is supplied into a reaction container which is arranged at an opposite direction of movement of the reaction containers.

Alternatively, it is solved in such a way that after washing liquid is sucked from a reaction container by a washing nozzle, the reaction container is moved while the washing nozzle retains therein the sucked-up washing liquid, and then, the washing liquid is discharged into another reaction container from the washing nozzle.

Alternatively, it is solved in such a way that after washing liquid is sucked from a reaction container by a washing nozzle, the washing liquid is temporarily reserved in storage parts, and after the reaction containers are moved, the washing liquid temporarily reserved in the storage parts is discharged into the reaction containers.

Alternatively, in the case of the provision of a washing pump for sucking up reacted liquid or washing liquid from a reaction container, it is solved in such a way that the washing pump is provided with a storage means in which sucked up reacted liquid or washing liquid is temporarily reserved, and a washing pipe connecting between the storage means and the reaction container washing means, for allowing reacted liquid or washing liquid to flow therethrough, a connection part of the washing pipe on the storage means side, being provided in the storage means at a level which is below the liquid surface of reaction liquid or washing liquid.

Alternatively, in the case of the provision of the above-mentioned storage means, it is preferable to set the capacity of the storage means which is larger than at least a quantity of washing liquid which is required for once washing the reaction container.

Alternatively, it is preferable to carry out measurements of a cell blank for a plurality of reaction container during washing in order to evaluate a concentration of washing liquid.

BRIEF DESCRIPTION OF THE DRAWINGS

FIG. 11b is a side view illustrating the pump shown in FIG. 11a.

DESCRIPTION OF THE PREFERRED EMBODIMENTS

Referring to FIGS. 1 to 4, explanation will be hereinbelow made of an embodiment of an automatically analyzing apparatus according to the present invention.

Figure 1A:
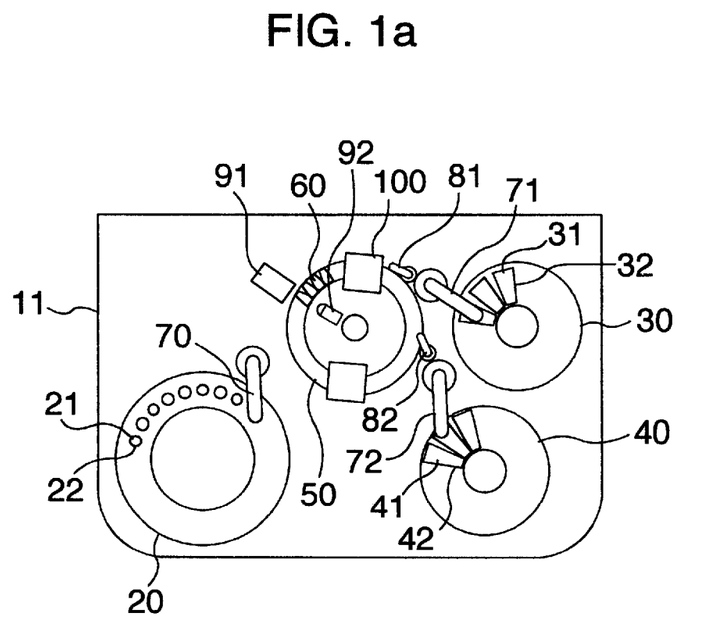
FIG. 1a is a top view illustrating an automatically analyzing apparatus according to the present invention.
Figure 1B:
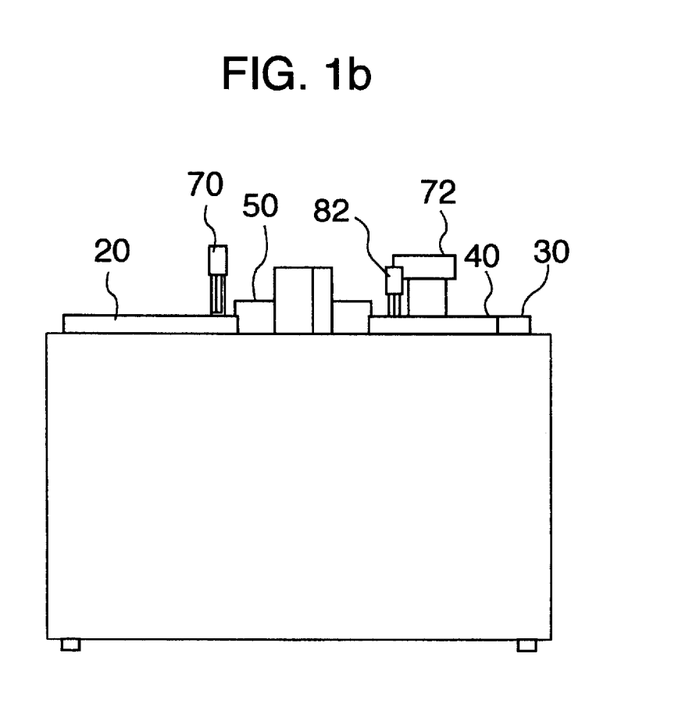
FIG. 1b is a front view illustrating an automatically analyzing apparatus according to the present invention.
Figure 2:
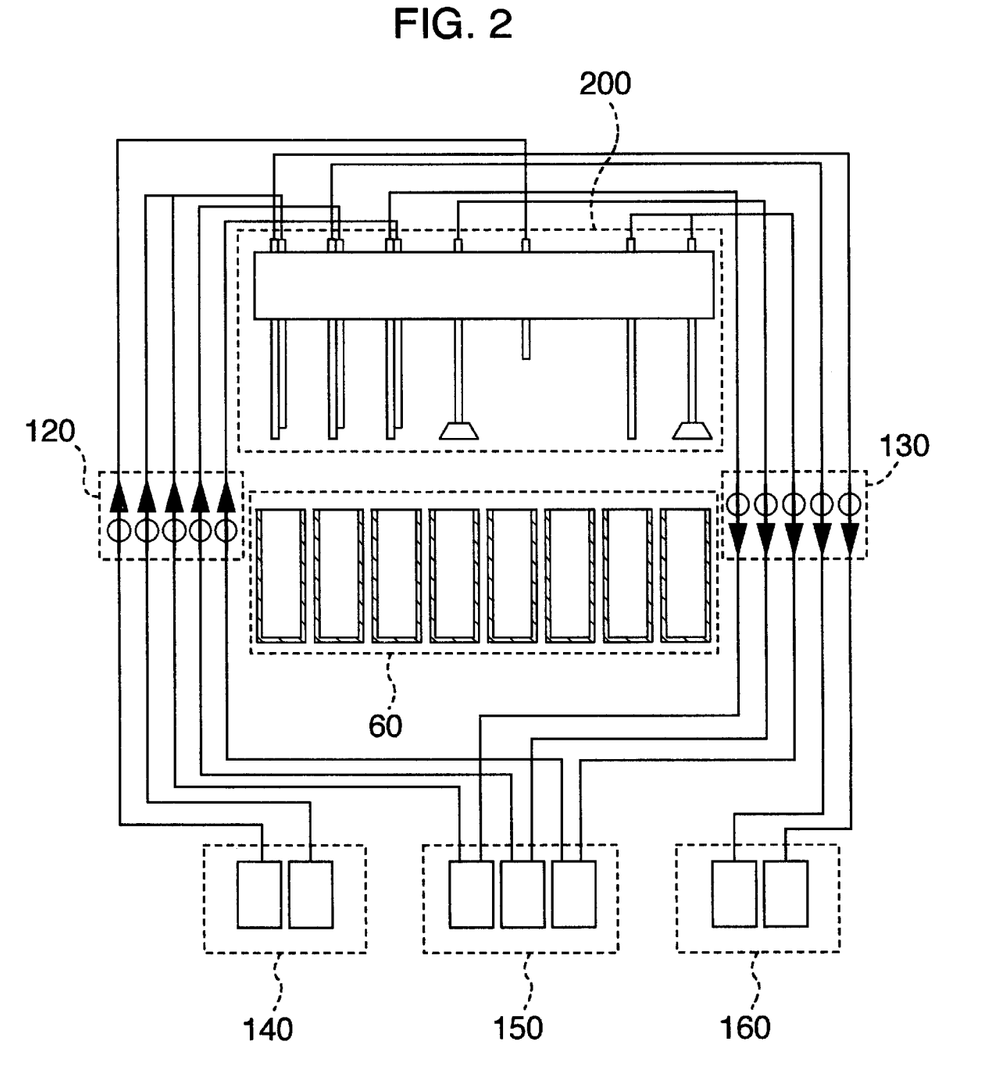
FIG. 2 is a structure view illustrating a reaction container washing means according to the present invention.
Figure 3:
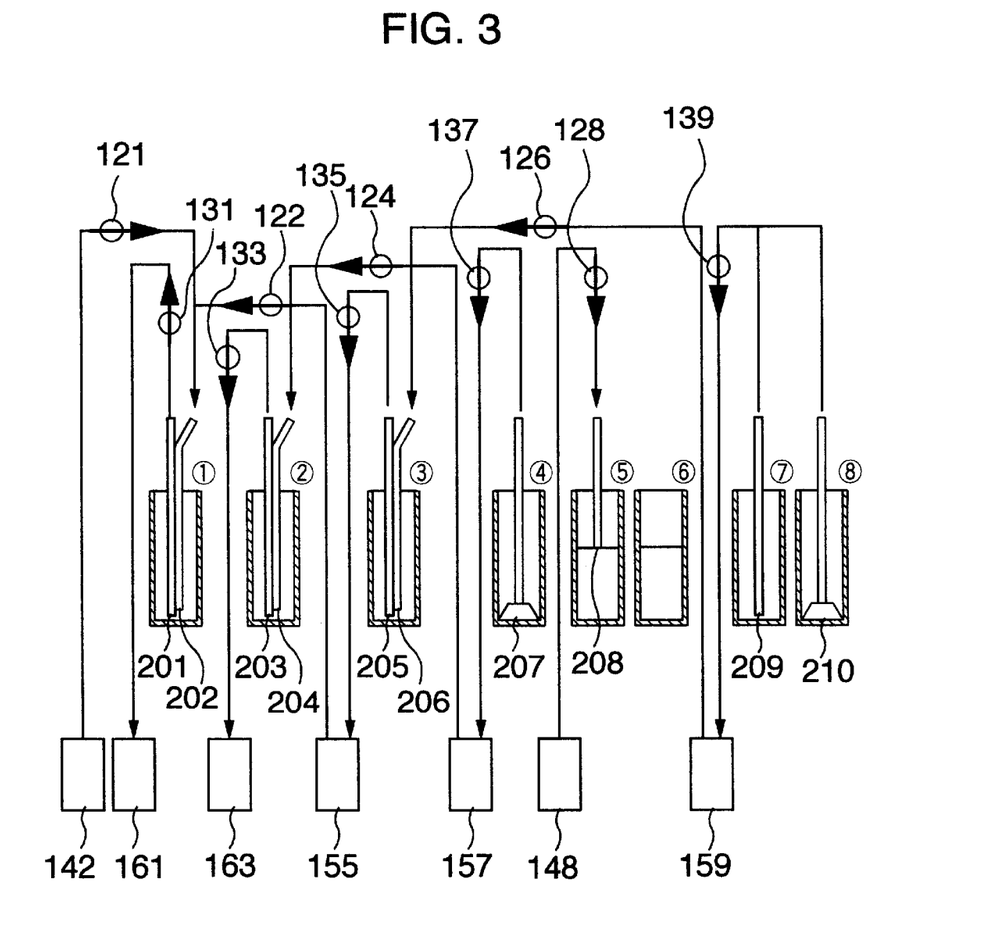
FIG. 3 is a view for explaining washing steps according to the present invention.
Figure 4:
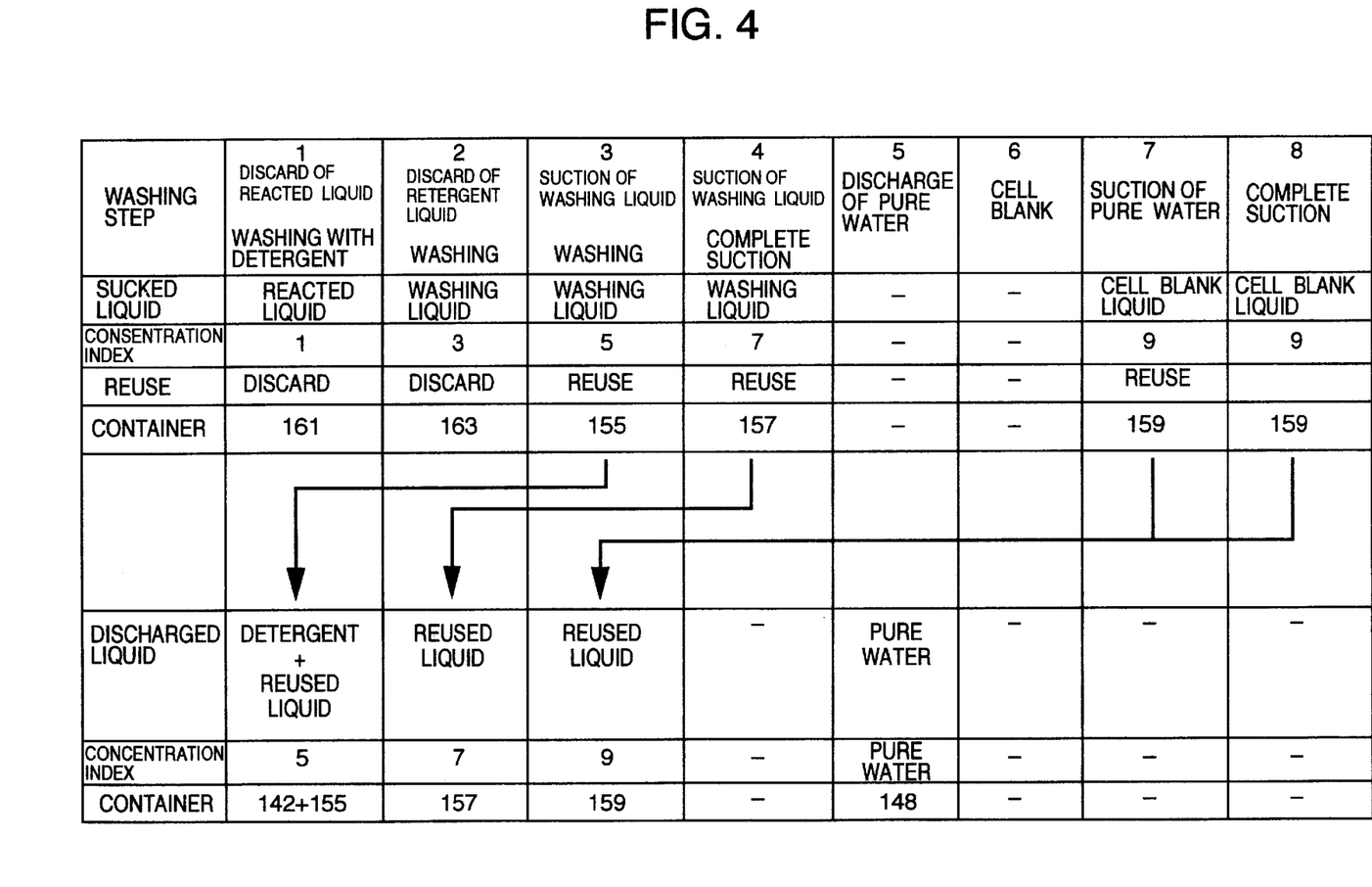
FIG. 4 is a view for explaining washing steps according to the present invention.

FIGS. 1a and 1b are overall structural views illustrating the automatically analyzing apparatus incorporating a reaction container washing machine (means) according to the present invention, and FIG. 2 is a structural view illustrating the reaction container washing machine according to the present invention while FIGS. 3 and 4 are views for explaining washing steps according to the present invention.

Referring to FIG. 1a and FIG. 1b which are top and front views illustrating the automatically analyzing apparatus, a plurality of sample containers 22 containing samples 21, are held so as to be circumferentially movable in a sample tank 20, and a plurality of first reagent containers 32 containing a first reagent 31 is held so as to be circumferentially movable in a first reagent tank 30. Similar to the first reagent tank 30, a plurality of second reagent containers 42 containing second reagent 41 are held so as to be circumferentially movable in a second reagent tank 40. Further, a plurality of reaction containers 60 is held so as to be circumferentically movable in a reaction tank 50.

There are arranged around the reaction tnak 50 a sample pipetter 70 for pipetting the sample 21 from the sample containers 22 into the reaction containers 60, and a first reagent pipetter 71 for pipetting the first reagent 31 from the first reagent containers 32 into the reaction containers 60, and a second reagent pipetter 72 for pipetting the second reagent 41 from the second reagent containers 42 into the reaction containers 60, a first stirring rod 81 for stirring reacted liquid in each of the reaction containers 60 just after the first reagent 31 is pipetted into the associated reaction container, a second stirring rod 82 for stirring reacted liquid in each of the reaction containers just after the second reagent 41 is pipetted into the associated reaction container 60, a spectrometer 91 and a lamp 92 for analyzing reacted liquid in a reaction container, and for measuring a cell blank thereof, and a means 100 for washing a reaction container.

Operation of this embodiment will be hereinbelow explained. The sample pipetter 70 sucks up a predetermined quantity of the sample 21 from one of the sample containers 22, and is discharged into a reaction container 60 located at a sample discharge position. The reaction container in which the sample 21 has been pipetted, is cicumferentially moved up to a first reagent discharge position within the reaction tank 50.

Then, the first reagent pipetter 71 sucks up a predetermined quantity of the first reagent 31 from one of the first reagent containers 32, and then discharges the same into the reaction container in which the sample 21 is pipetted. After the first reagent 31 is pipetted, the reaction container 60 is cirumferentially moved to a first stirring position in the reaction tank 50, and accordingly, the first stirring rod 81 stirs reacted liquid composed of the sample 21 and the first reagent 31. In the case of the necessity of addition of the second reagent, the reaction container 60 is circumferentially moved within the reaction tank 50 to a second reagent discharge position, and then, the second reagent pipetter 72 sucks up a predetermined quantity of the second reagent 41 from one of the second reagent containers 42, and discharges the same into the reaction container in which the reacted liquid composed of the sample 21 and the first reagent 31 is held.

Next, the reaction container 60 is circumferentially moved to a second stirring position within the reaction tank 50, and at this position, the second stirring rod 82 stirs the solution of the sample 21, the first reagent 31 and the second reagent 41. After the stirring, the sample 21 and the reagents gradually react together, and finally, the solution exhibits a color the degree of which corresponding to a concentration of a component to be examined. During progress of this reaction, the spectrometer 91 measures an absorption spectrum in accordance with transmitted light from the reaction container 60 onto which light from the lamp 92 is irradiated, in order to quantify a concentration.

After completion of the measurement, the reaction container 60 is moved to a washing position within the reaction tank 50, at which the reaction container 60 is washed by the reaction container washing means 100. After completion of the washing, the reaction container is returned to the sample discharge position, and subjected to the repetition of the pipetting of the sample, the pipetting of the reagents, the analysis and the washing.

Referring to FIG. 2 which shows the overall structure of the reaction container washing machine, this reaction container washing machine is composed of: a nozzle part 200 composed of a discharge nozzle for discharging washing liquid into one of the reaction containers 60 and a suction nozzle for sucking up reacted liquid or washing liquid from the reaction container, a discharge pump part 120 and a suction pump part 130, a supply container part 140 for reserving pure water for washing, and detergent, a reuse container part 150 for respectively reserving washing liquid having different concentrations of reacted substance after washing, a waste container part 160 for discarding reacted liquid and washing liquid having a high concentration of reacted substance which had been analyzed, after washing, and pipe lines connecting among the container parts, the pump part and the nozzle part.

Referring to FIGS. 3 and 4, explanation will be made of washing steps of the reaction container washing machine shown in FIG. 2. It is noted that FIG. 3 is a view illustrating several components of the reaction container washing liquid shown in FIG. 2 which are arranged successively along with respective washing steps. Further, FIG. 4 is a chart of the washing steps.

The washing steps are eight steps, that is first step to eighth steps, and different washing nozzles, pumps, containers are used for the washing steps, respectively. The washing nozzles and the washing steps correspond to each other one-to-one, and the reaction containers comes to a stop, successively, at the positions of the washing nozzles in order to carry out the washing steps 1 to 8.

FIG. 4 shows indices indicating concentrations of reacted substance in sucked and discharged liquid at the respective washing steps for convenience's sake of the explanation. As will be explained latter, the concentration of reacted substance in the washing liquid is lowered by about two order at every washing steps, there are set washing liquid having a concentration index of 3 after completion of the first washing step, a concentration index of 5 after completion of the second washing step, a concentration index of 7 after completion of the third washing step, and a concentration index of 9 after completion of the fourth washing step, the larger the number of the washing step, the lower the concentration if the concentration index of the reacted liquid is estimated to be 1. Next, explanation will be made of washing operation at each of the washing steps:

Washing Step 1: reaction liquid after completion of analysis is sucked up by a suction nozzle 201 and a liquid suction pump 131 and is discarded into a reaction liquid waste container 161. Then, detergent liquid is fed by a discharge pump 121 into a supply nozzle 202 from a detergent supply container 142, and simultaneously, reuse liquid having a concentration index of 5 is fed into the supply nozzle 202 from a reuse container 155 by a supply pump 122 so as to dilute the detergent liquid in order to obtain washing liquid which is then discharged into the reaction container. Then, liquid containing reacted substance having been not sucked up by the suction nozzle 201 and remaining in the reaction container through previous operation is solved into this washing liquid during the present washing step, and accordingly, the washing liquid has a concentration index of about 3.

Washing Step 2: the washing liquid solved therein with the reacted substance and the detergent liquid at the washing step 1, and having the concentration index of 3 is sucked up by a suction nozzle 203 and a suction pump 133 and is then discarded into a liquid waste container 163 for washing liquid having a concentration index of 3. Then, washing liquid having a concentration index of 7 is discharged from a reuse container 157 into the reaction container by a supply nozzle 204 and a supply pump 124. Accordingly, liquid having been not sucked up by the nozzle 203 and remaining in the reaction container is solved into the washing liquid having the concentration index of 7. Thus, the washing liquid has a concentration index of about 5.

Washing Step 3: the washing liquid having the concentration index of 5 obtained at the washing step 2 is sucked up by a suction nozzle 205 and a suction pump 135, and is reserved in a reuse container 155. Then, washing liquid having a concentration index of 9, which is reusable, is discharged into the reaction container from a reuse container 159 by a supply nozzle 206 and a supply pump 126. The liquid having been not sucked up by the suction nozzle 205 and remaining in the reaction container is solved into the washing liquid having the concentration index of 9. Thus, the washing liquid has a concentration index of about 7.

Washing Step 4: the washing liquid having the concentration index of 7 obtained at the washing step 3 is sucked up by a suction nozzle 207 and a suction pump 137, and is then reserved in a reuse container 157. The suction nozzle 207 is capable of sucking up the washing liquid which is likely to remain in every nook and corner of the bottom surface of the reaction container, and accordingly, the liquid can hardly remain in the reaction container. However, if the liquid remains by a slight amount, this liquid remains in the reaction container until the next washing step 5.

Washing step 5: pure water is discharged from the pure water supply container 148 into the reaction container in order to measure a cell blank by means of a supply nozzle 208 and a supply pump 128. In such a case that liquid containing the reacted substance has remained by a slight quantity in the reaction container after completion of the washing step 4, the liquid containing the remaining reacted substance is solved into the pure water. Thus, the cell blank liquid into which the reacted substance is solved by a slight quantity has a concentration index of 9.

Washing Step 6: A cell blank is measured.

Washing Step 7: The cell blank liquid having the concentration index of 9 is sucked up by a suction nozzle 209 and a suction pump 139, and is reserved in a reuse container 159 for liquid having a concentration index 9.

Washing step 8: the cell blank liquid having the concentration index 9 having been not sucked up and remaining at the washing step 7 is completely sucked up by a suction nozzle 210 and a suction pump 139, and is reserved in the reuse container 159 having a concentration index 9.

With the use of the above-mentioned washing steps, the washing for one reaction container can be made through the supply of pure washing liquid to be used for washing only by one time at the washing step 5. Used washing liquid is reused for the remaining washing steps, and only washing liquid having a concentration index of 3 and having been reused by three times, and reacted liquid used for analysis and having a concentration index of 1 are finally discarded during the washing steps. It goes without saying that only pure washing liquid is used when the washing is carried out at the first time, since no used washing liquid is present.

Further, it is noted that, in a conventional reaction container washing means, fresh washing liquid is used at each washing step. Accordingly, the reaction container washing liquid according to the present invention can reduce the consumption of washing liquid down to one-fourth of that used in the conventional reaction container washing means. Further, the quantity of waste liquid to be discarded can be reduced in comparison with that of the conventional one, thereby it is possible to reduce the problem of environmental contamination.

Next, explanation will be made of how the degree of cleanliness or the concentration of washing liquid vary by reducing the consumption of washing liquid with the reuse of washing liquid.

Figure 5:
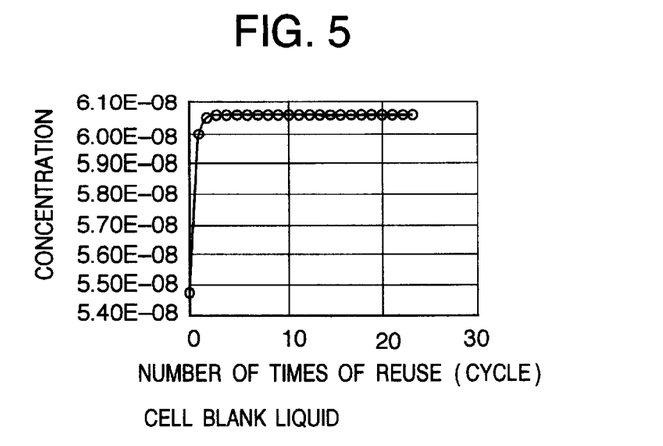
FIG. 5 is a view showing results of calculation of washing effects according to the present invention.

FIG. 5 is a graph which shows results of calculation for variation in the concentration of cell blank liquid which is sucked through the washing steps 7, 8 in consideration with the reuse of the washing liquid. For this calculation, the estimation is made such that 5% of washing liquid cannot be sucked by any one of usual suction nozzles 201, 203, 205, and remains in a reaction container while 1% of washing liquid cannot be sucked up by the nozzle 207 which can suck up washing liquid from the corner parts of the bottom surface of the reaction container, and remains in the reaction container. At first, the calculation is made for the case of using pure water as cleaning liquid in an initial condition, and the concentration of thus obtained cell blank liquid is set to that of the washing liquid which is reused by zero time. The results of the calculation are plotted in FIG. 5. During the process of this calculation, since the concentration of the reused washing liquid can be obtained each washing step, the calculation of the concentration of the cell blank liquid is made such that the reused washing liquid is used as washing liquid in next washing. That is, this is the result of the reuse of the washing liquid at the first time.

Similarly, from the concentration of the reused washing liquid obtained at each washing step, subsequent concentrations of cell blank liquid are calculated one by one as the number of times of reuse increases. From the figure, it can be understood that the concentration of the washing liquid becomes substantially constant after the washing liquid being reused by a number of times. That is, even though the number of times for reuse is increased, the concentration of the washing liquid which has been reused does not exceeds a predetermined value. Since the concentration of reacted liquid at the first time is set to 0.1 g/L, the concentration of the cell blank liquid is smaller than that of the reacted liquid by more than 6 figures, thereby it is possible to exhibit a sufficient cleaning effect even though the reused washing liquid is used for washing.

Figure 6:
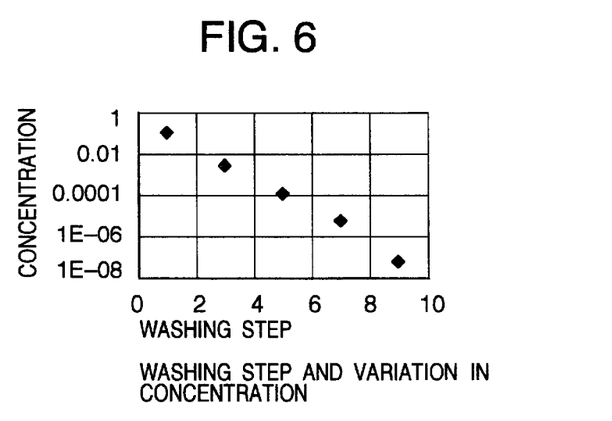
FIG. 6 is a view showing results of calculation of washing effects according to the present invention.

FIG. 6 shows the concentrations of washing liquid obtained at the respective washing steps. Similar to the cell blank liquid, the concentration of washing liquid obtained at each washing step becomes constant after being used by a number of times. This value is plotted with logarithmic scales. It can be understood that the concentration of the washing liquid decreases exponentially as the number of washing steps increases. With the use of the reaction container washing means according to the present invention, since the supply of washing liquid is made only one time for washing each reaction container, even though the number of washing steps is increased, the quantity of the washing liquid does not increase, thereby it is possible to enhance the degree of accuracy for washing.

Figure 7:
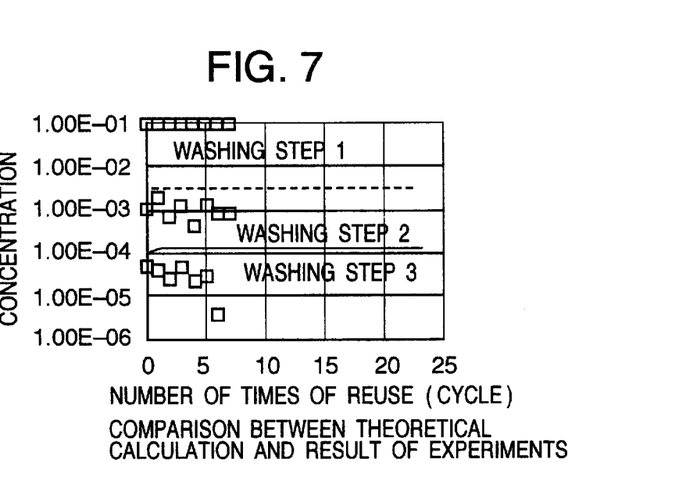
FIG. 7 is a view showing results of comparison between washing effects obtained by theoretical calculation and results of experiments.

FIG. 7 exhibits the comparison between the results of the theoretical calculation and results of experiments. In the experiment, the absorbency of washing liquid sucked from the reaction container was measured by a spectrometer, and the thus measured value was converted into a concentration. Similar to the results of the theoretical calculation, the concentration of the washing liquid does not exceed a predetermined value even though the number of times of reuse increases. Substantially no variation in the concentration of the washing liquid is appreciated even though it is compared with the one in such a case that the number of times for reuse is zero, that is, washing is made with the use of pure water. Thus, with the use of the reaction container washing means according to the present invention, the consumption of washing liquid can be reduced while the conventional washing capacity is held.

It is noted that an equal quantity of washing liquid is used at each washing step, the taken-in and -out quantities of liquid of the reuse containers 155, 157, 159 to and from the reaction container becomes substantially equal to one another. Accordingly, the quantity of reused washing liquid reserved in each of the reuse containers 155, 157, 159 may be at least equal to a quantity for washing a reaction container by one time. Further, the volume of each of the reuse containers 155, 157, 159 may be larger than at least a quantity for washing a reaction container by a one time.

Figure 8:
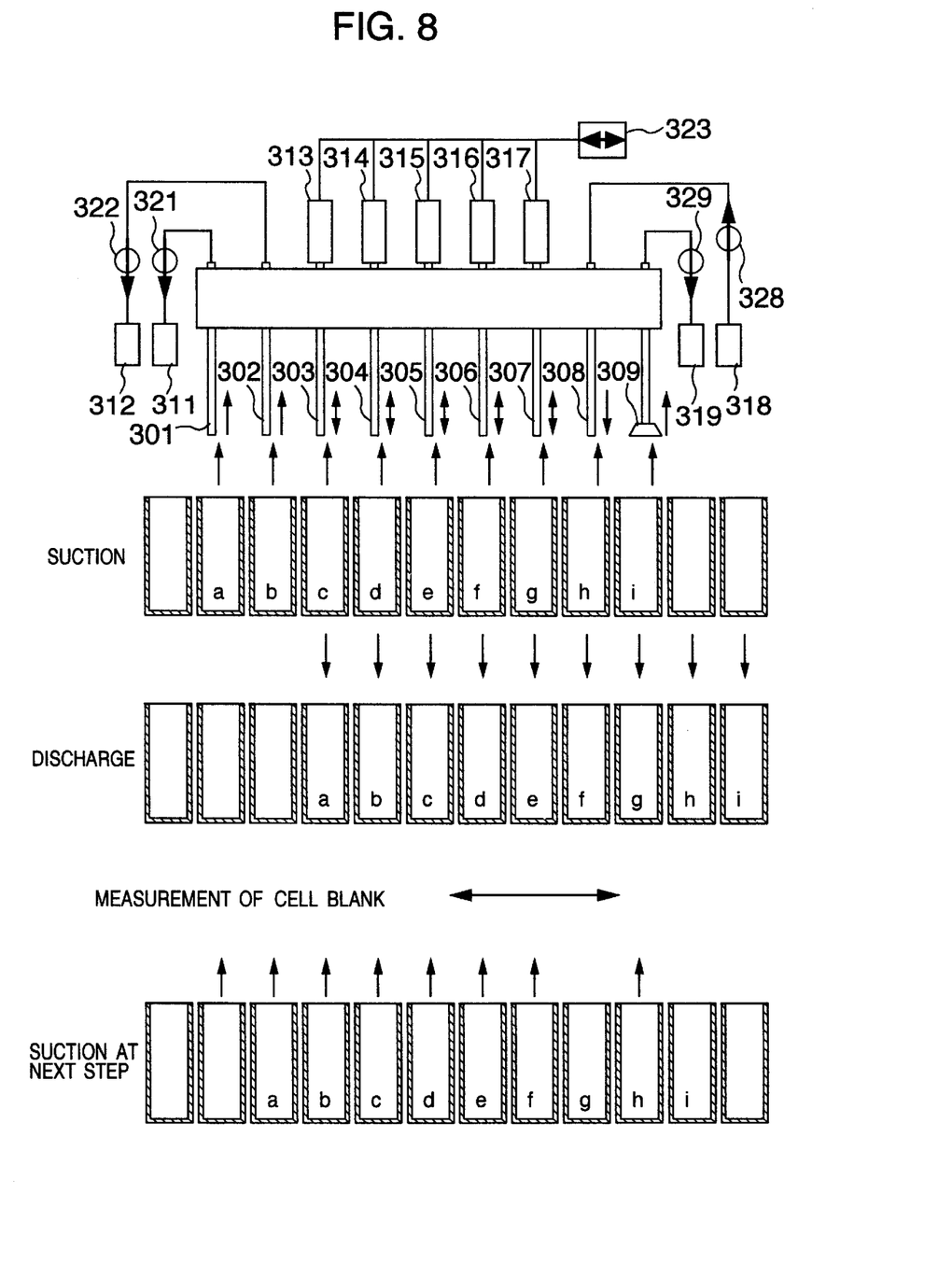
FIG. 8 is a structural view illustrating the reaction container washing means according to the present invention, for explaining the washing steps.

Referring to FIG. 8, explanation will be made of a second embodiment of the washing means in the automatically analyzing apparatus according to the present invention.

A washing means shown in FIG. 8 incorporates washing nozzles 301 to 309 for sucking or discharging reacted liquid or washing liquid to and from a reaction container. The suction nozzle 301 sucks up reacted liquid from the reaction container by driving a suction pump 321, and discharges the reacted liquid into the reacted liquid waste container 311. The suction nozzle 302 sucks up washing liquid from the reaction container by driving a suction pump 322, and discharges the same into a waste washing liquid container 312. The suction nozzle 303 to 307 suck up washing liquid from the reaction containers by driving a suction and discharge pump 323, and thus sucked up washing liquid is temporarily reserved in washing liquid storage containers 313 to 317. Then, the thus reserved washing liquid is discharged as washing liquid into the reaction container. The discharge nozzle 308 discharges pure water into the reaction container from a pure water supply container 318 by driving a discharge pump 328. The suction nozzle 309 sucks up washing liquid from the reaction container, and discharge the same into the waste washing liquid container 319 by driving a suction pump 329.

Explanation will be made of the operation of the suction or suction/discharge nozzles and the reaction containers. Estimation is made such that nine reaction containers a to i come to a stop at the positions of the nozzles 301 to 309, respectively. The nozzles carry out suction, and accordingly, the suction nozzles 301 and 302 suck up reacted liquid and washing liquid from the reaction containers a and b, respectively, and discard them into the waste reacted liquid containers 311 and the waste washing liquid container 312. The suction/discharge nozzles 303 to 307 suck up washing liquid from the reaction containers c to g, and temporarily reserve the same in the washing liquid storage containers 313 to 317. At this time, the discharge nozzle 308 does not perform suction since it is exclusively used for supplying pure water.

The suction nozzle 309 is capable of sucking up washing liquid remaining even in corner parts of the bottom surface of the reaction container, and thus sucked up washing liquid is discharged into the waste washing liquid container 319. After completion of the suction, the reaction containers are turned so that the reaction container a comes to the position of the washing nozzle 303. At this time, discharge operation is started. The suction nozzles 303 to 307 discharge washing liquid having been temporarily reserved in the washing liquid storage containers into reaction cells a to e.

The discharge nozzle 308 discharges pure water into the reaction container f. Next, the reaction containers are turned by about one revolution so that the reaction container a comes to the position of the suction nozzle 302 in order to repeat the suction and discharge operation as mentioned above. During rotation from the discharge operation to the suction operation, cell blanks for the reaction containers d to f are measured.

With the repetitions of the above-mentioned suction and discharge operation, the reaction containers are all washed one by one. External supply of washing liquid is only made by the discharge nozzle 308 for discharging pure water. Namely, the washing liquid is reused by all the other nozzles. It is important that the washing liquid should be reused successively for the containers ranging from the one in which liquid is contaminated by a thin concentration to the one in which liquid is contaminated by a thick contamination. Further, the thicker the concentration of contamination in the liquid within the reaction container, the smaller the quantity of washing liquid is used in order to prevent the reacted substance from remaining in the upper part of the inner wall of the reaction container.

The measurement of a cell blank is carried out for three containers in this embodiment. Inherently, the measurement of a cell blank is carried out by discharging pure water into a reaction container which has been already washed. In this embodiment, all cell blanks by three times are measured by changing cell blank liquid for each time on the way of the progress of the washing steps. The reaction container for which the cell blank is started has been subjected to washing steps by a number equal to that of the conventional one, and thus, the cleanliness is sufficient. Accordingly, washing liquid used for cell blanks by three times is sufficiently clean.

It is noted that since the reuse liquid is used as washing liquid in this embodiment, the cell blank is used for managing the concentration of the reuse liquid. For example, if the value of a cell blank at a first time differs from that at a second time or a time thereafter, warning informing of contamination of washing liquid is issued, and if the value of a cell blank at the second time is also abnormal, the display of the necessity of replacement of washing liquid and so forth is made for countermeasures.

Figure 9:
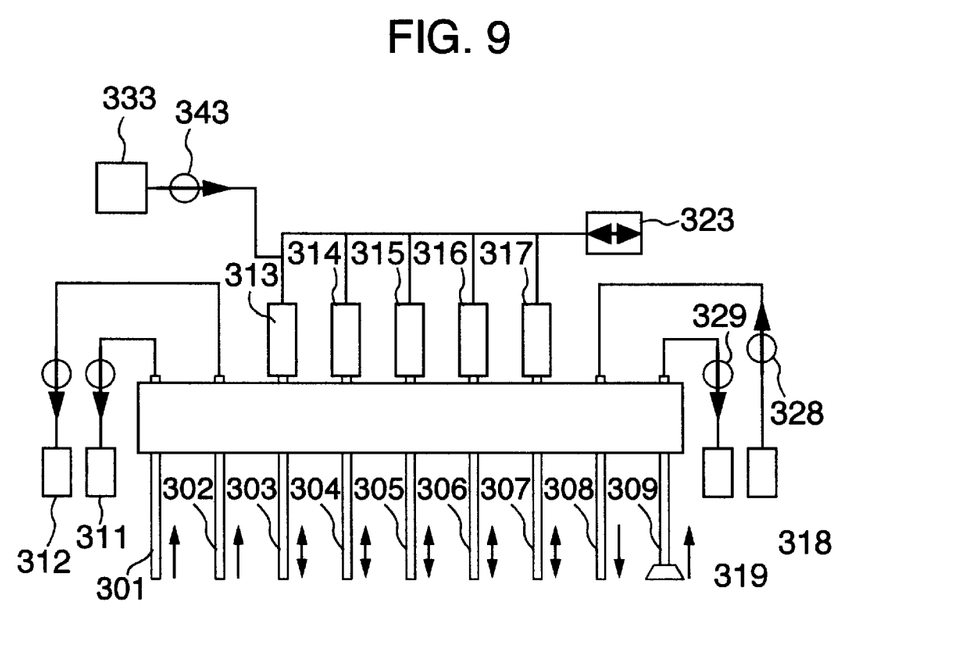
FIG. 9 is a structural view illustrating the reaction container washing means according to the present invention.

In the embodiment shown in FIG. 8, no detergent is used for washing the reaction containers. However, the detergent may be used as shown in FIG. 9. Referring to FIG. 9, the detergent is supplied into the washing liquid storage container 313 from a detergent supply container 333. The detergent is diluted by washing liquid within the washing liquid storage container 313, and is then discharged into the reaction container.

In this embodiment, when the washing liquid is reused, the washing liquid having the same concentration is sucked up and discharged by one and the same nozzle since the position of the reaction container is shifted between the time when the washing liquid is sucked up and the time when the washing liquid is discharged. Accordingly, it is sufficient to temporarily reserve the washing liquid after suction, into a small storage container connected to the nozzle. Thus, the structure may be simplified, and the volume of the storage container may be at least larger than a quantity of discharge by one time.

Figure 10:
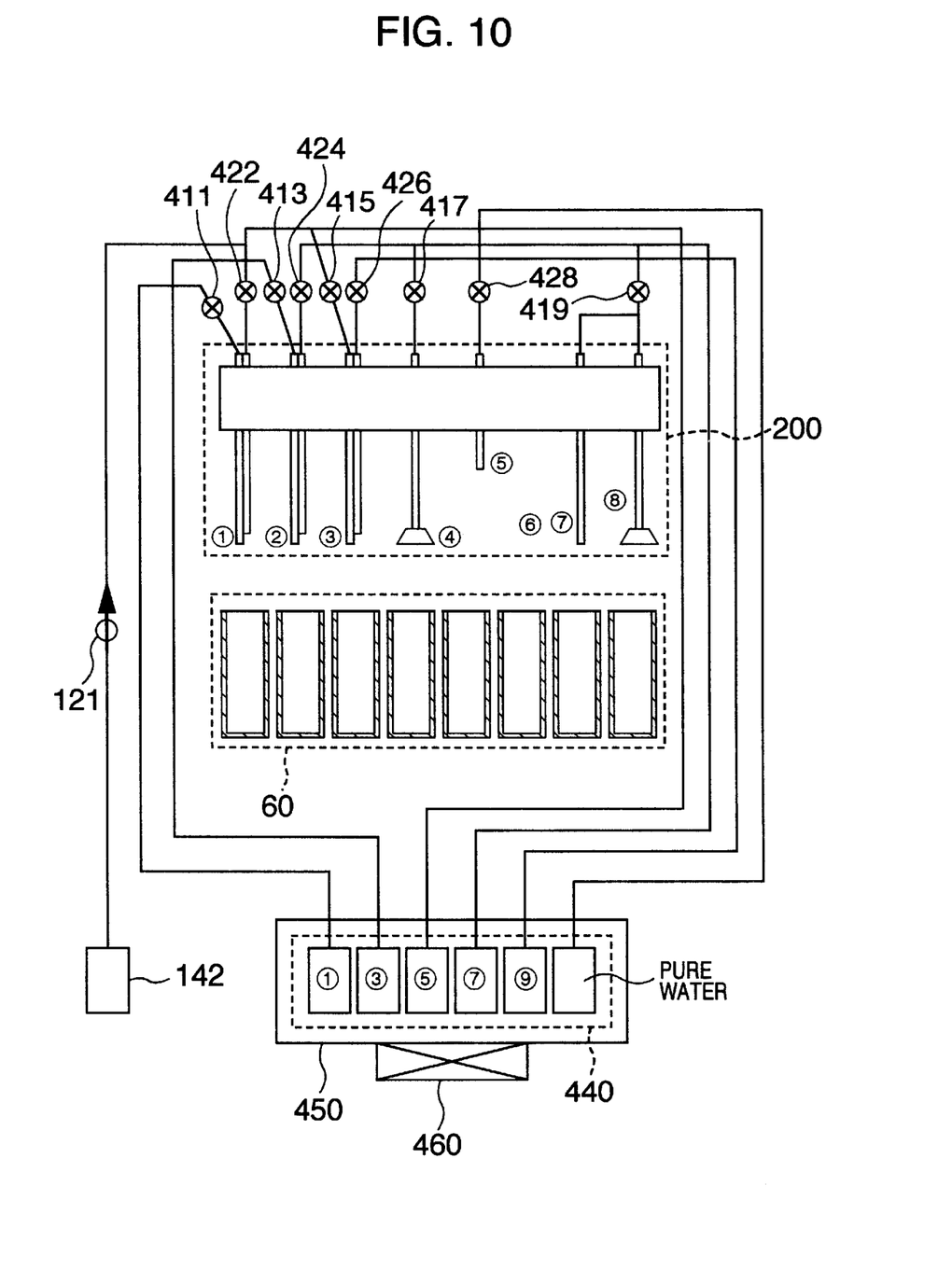
FIG. 10 is a structural view illustrating the reaction container washing means according to the present invention.

Referring to FIG. 10, explanation will be made of a third embodiment of the automatically analyzing apparatus according to the present invention.

A reaction container washing machine shown in FIG. 10, comprises a nozzle part 200 for discharging washing liquid into the containers 60 and for sucking reacted liquid or washing liquid from the reaction containers, a reuse pump part 450, a detergent supply part 142, a detergent discharge pump 121, suction valves 411, 413, 415, 417, 419, and discharge valves 422, 424, 426, 428. The reuse pump part 450 incorporates a reuse container part 440 and a fan 460. The reuse pump part 450 incorporates a suction mode in which reacted liquid or washing liquid is sucked up from a reaction container, and a discharge mode in which washing liquid is discharged into a reaction container, either one of the modes being selected by changing over a valve provided in the pump part 450. In the reuse container part 440, the reacted liquid and washing liquid are sorted in accordance with their concentration. Numbers attached to the containers indicate concentrations defined similar to those shown in FIG. 4. The reuse pump part 450 will be detailed later with reference to FIG. 11.

Eight washing steps, that is, washing steps 1 to 8 are carried out in this embodiment. Nozzles and the washing steps correspond to each other one-to-one. Each time when the reaction containers come to a stop at the positions of the nozzles, successively, the washing steps 1 to 8 are carried out. Explanation will be hereinbelow made of the washing mechanism at each of the washing steps.

Washing Step 1: the reuse pump part 450 is set in the suction mode, and the suction valve 411 is opened so that reacted liquid from a reaction container after analysis is sucked up, and is discharged into the reuse container 440. Then, the pump part 450 is set in the discharge mode, and the discharge valve 422 is opened so that washing liquid having a concentration index 5 is discharged into the reaction container, and simultaneously, detergent is discharged into the reaction container from the detergent supply container 142 by the discharge pump 121. Reacted substance remaining in the reaction container is solved into the washing liquid which therefore has a concentration index 3;

Washing Step 2: the pump part 450 is set in the suction mode, and the suction valve 413 is opened so that the washing liquid having the concentration index of 3 obtained at the washing step 1 is sucked up from the reaction container, and is discharged into the reuse container 440. Next, the pump part 450 is set in the discharge mode, and the discharge valve 424 is opened so that washing liquid having a concentration index 7 is discharged into the container. Reacted substance remaining in the reaction container is solved in the washing liquid which therefor has a concentration index 5;

Washing Step 3: the pump part 450 is set in the suction mode, and the suction valve 415 is opened so that the washing liquid having the concentration index of 5 obtained at the washing step 2 is sucked up from the reaction container, and is discharged into the reuse container 440. Next, the pump part 450 is set in the discharge mode, and the discharge valve 426 is opened so that washing liquid having a concentration index 9 is discharged into the container. Reacted substance remaining in the reaction container is solved in the washing liquid which therefor has a concentration index 7;

Washing step 4: The pump part 450 is set in the suction mode, and the suction valve 417 is opened so that the washing liquid having the concentration index 7 obtained at the washing step 3 is sucked up from the reaction container, and is discharged into the reuse container 440;

Washing Step 5: the pump part 450 is set in the discharge mode, and the discharge valve 428 is opened so as to discharge pure water into the reaction container. Reacted substance remaining in the reaction container is solved into the washing liquid which therefore has a concentration index of 7. If the reacted substance remains after completion of the step 4, reacted substance is solved in the pure water which therefore has a concentration index of 9;

Washing Step 6: a cell blank is measured;

Washing Step 7: the pump part 450 is set in the suction mode, and the suction valve 419 is opened so that the cell blank liquid having the concentration index of 9 is sucked up from the reaction container and is then discharged into the reuse container 440;

Washing Step 8: the cell blank liquid having the concentration index of 9 having been not yet sucked up at the washing step 7 and remaining is again sucked up from the reaction container, and is discharged into the reuse container 440.

As mentioned above, similar to the first embodiment, with the use of the above-mentioned washing steps, the supply of the washing liquid to be used for washing may be made by only one time for washing one reaction container, at the washing step 5 at which the pure water is supplied. Reuse liquid is used as the washing liquid at any of the remaining washing steps. Further, only the washing liquid having a concentration index of 3 which has be reused by three times, and reacted liquid having a concentration index 1 are finally discarded through the all washing steps.

Figure 11A:
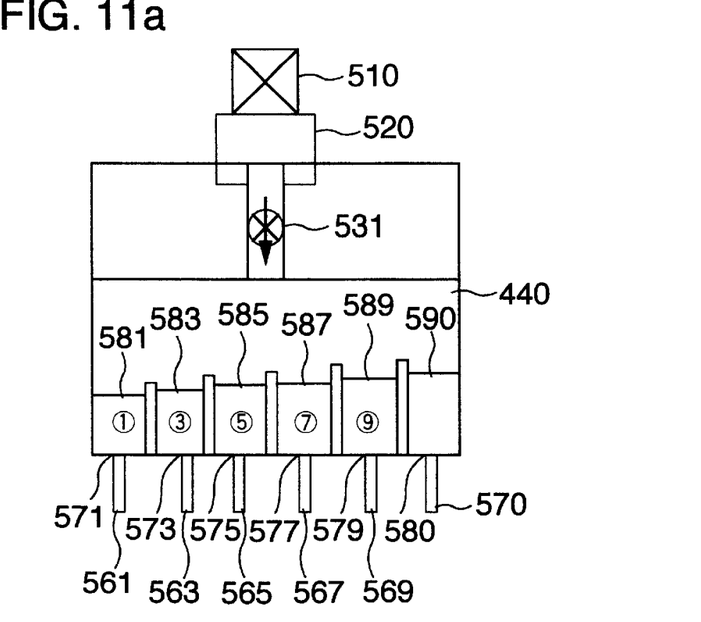
FIG. 11a is a front view illustrating a pump for reuse, according to the present invention.
Figure 11B:
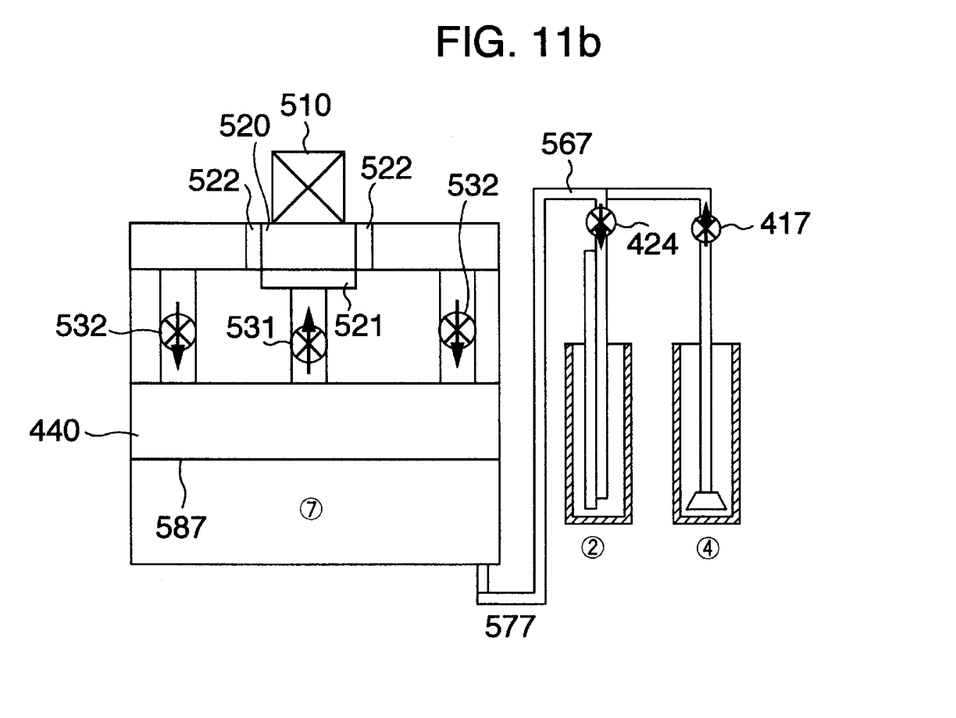

This embodiment is substantially identical with the first embodiment, except that this embodiment uses the pump part 450. FIG. 11a and FIG. 11b are side views illustrating the reuse pump part as viewed in two different directions, respectively.

The reuse pump part 450 incorporates a drive motor 510, a fan 520, and a reuse container 440, a suction valve 531 and a discharge valve 532.

Explanation will be hereinbelow made of the operation of the pump part 450. When the fan 520 is driven by the drive motor 510, air is sucked up through an intake port 521, and air is discharged from a discharge port 522. When the suction valve 531 is opened while the discharge valve 532 is closed, a suction mode is set up. Meanwhile, when the suction valve 531 is closed while the discharge valve 532 is opened, a discharge mode is set up. In the suction mode, the pressure in the reuse container 440 lowers so that washing liquid is sucked up from the reaction container through pipe lines 561 to 570. In the discharge mode, the pressure of the reuse container 440 increases so that the washing liquid is discharged into the reaction container through the pipe line 567.

Referring to FIG. 11b which shows the reaction containers at the washing steps 2 and 4 which have been explained with reference to FIG. 10. In such a case that the washing liquid is sucked up at the washing step 4, the pump part 450 is set in the suction mode, and the suction valve 417 is opened while the discharge valve 424 is closed. At the washing step 4, the washing liquid having the concentration index of 7 is reserved in a container exclusive for the concentration index of 7, which is partitioned within the reuse container 440.

Then, in such a case that the washing liquid is discharged into the reaction container at the washing step 2, the reuse pump part 450 is set in the discharge mode, and the discharge valve 424 is opened while the suction valve 417 is closed. The washing liquid reserved previously and having the concentration index of 7 is discharged into the reaction container at the washing step 2. The reuse container 440 is partitioned into sections respectively for different concentration indices, and the pipe lines 561 to 570 through which washing liquid is sucked up and discharged, are connected to the sections, respectively, for the different concentration indices.

Connecting parts 571 to 580 of the pipe lines connected to the reuse container 440 are set below the liquid surfaces 581 to 590 of washing liquid which are sorted for different concentration indices. When the washing liquid is sucked up from the reaction container, air is sucked up simultaneously, and accordingly, should the connecting parts be higher than the liquid surfaces of washing liquid, droplets of slight washing liquid would be mingled into air, and be then sucked into the fan 520. With the provision of the connecting parts within the washing liquid, it is possible to prevent the fan 520 from being contaminated by washing liquid.

With the provision of the reuse pump part according to the present invention in a washing mechanism, no pumps for suction and discharge are required for the respective washing nozzles. Thereby it is possible to make the washing mechanism small-sized. Since the washing liquid for every washing nozzle is reused, the capacity of the container in which washing liquid having any of different concentration indices is contained, may be set to a value which is equal to the quantity of washing liquid by one washing time.

According to the present invention, the washing liquid used in for washing the reaction container, is reused, for different concentration indices of reacted substance, thereby it is possible reduce the consumption of washing liquid without deteriorating the cleanliness. Further, since the consumption of washing liquid is not increased even though a washing step is further added, washing steps can be added as necessary in order to enhance the cleanliness. Further, the quantity of waste liquid to be discarded can be reduced, thereby it is possible to reduce environmental contamination.

What is claimed is:

1. An automatically analyzing apparatus, comprising:
   a plurality of reaction containers for reacting a sample with a reagent; and
   a reaction container washing unit for washing the reaction containers through a plurality of successive washing stations, said reaction container washing unit including:
      a first washing station for feeding a washing liquid from a washing station downstream of the first washing station into each of the reaction containers after a reacted content containing a reacted substance is discharged from the reaction container, so as to obtain a washing liquid having a concentration of the reacted substance $(C_1)$,
      a second washing station for discharging the washing liquid having the concentration $(C_1)$ from the reaction container into a second station reuse container belonging to the second washing station, and feeding a washing liquid from a washing station downstream of the second washing station into the reaction container so as to obtain a washing liquid having a concentration of the reacted substance $(C_2$, wherein $C_2 < C_1)$,
      a plurality of intermediate washing stations each for discharging a washing liquid having a concentration of the reacted substance one of $(C_2 \ldots C_{n-1}$, wherein n equals an integer) from the reaction container into a reuse container belonging to each intermediate washing station, and feeding washing liquid from a station downstream thereof into the reaction container so as to obtain a washing liquid having a concentration of the reacted substance one of $(C_3 \ldots C_{n-1})$,
      one of said plurality of intermediate washing stations being a latter stage washing station for discharging a washing liquid having a concentration of the reacted substance $(C_{n-1})$ from the reaction container into a latter stage reuse container belonging thereto, and feeding a pure washing liquid into the reaction container so as to obtain a washing liquid having a concentration of the reacted substance $(C_n)$, and
      a final washing station for discharging a washing liquid having a concentration of the reacted substance $(C_n)$ from the reaction container into a final station reuse container belonging thereto,
   wherein the washing liquid fed into the reaction container at each washing station is fed from the reuse container belonging to a washing station downstream thereof, and the concentration of the reacted substances $(C_1, C_2, C_3 \ldots C_{n-1}, C_n)$ are successively lower.

2. An automatically analyzing apparatus as set forth in claim 1, wherein the reaction container at each of the washing stations, except the latter stage and final washing station, is fed with the washing liquid from the reuse container belonging to a washing station one downstream from the next washing station downstream thereof.

3. An automatically analyzing apparatus as set forth in claim 1, wherein each washing station includes a supply nozzle for feeding the washing liquid from the reuse container belonging to a washing station downstream thereof through a communication passage which is laid below a surface level of the washing liquid reserved in the reuse container.

4. An automatically analyzing apparatus, comprising:
   a plurality of reaction containers for reacting a sample with a reagent; and
   a reaction container washing unit for washing the reaction containers through a plurality of successive washing stations, said reaction container washing unit including:
      a first washing station for feeding a reacted liquid from each of said plurality of reaction containers, after completion of analysis, and then feeding a detergent agent, from a detergent supply container, and a washing liquid from a washing station downstream of the first washing station, into the reaction containers in order to dilute a liquid containing reacted substance remaining in the reaction container, so as to obtain a washing liquid having a concentration of the reacted substance $(C_1)$,
      a second washing station for discharging the washing liquid having the concentration $(C_1)$ from the reaction container into a second station reuse container belonging to the second washing station, and feeding a washing liquid from a washing station downstream of the second washing station into the reaction container so as to obtain a washing liquid having a concentration of the reacted substance $(C_2$, wherein $C_2 < C_1)$,
      a third washing station for discharging the washing liquid having the concentration $(C_2)$ from the reaction container into a third station reuse container belonging to the second washing station, and feeding a washing liquid from a washing station downstream of the third washing station into the reaction container so as to obtain a washing liquid having a concentration of the reacted substance $(C_3$, wherein $C_3 < C_2)$,
      a plurality of intermediate washing station for discharging a washing liquid having a concentration of the reacted substance one of $(C_4 \ldots C_{n-1}$, wherein n equals an integer) from the reaction container into a reuse container belonging to each washing station, and feeding washing liquid from a station downstream thereof into the reaction container so as to obtain a washing liquid having a concentration of the reacted substance one of one of $(C_5 \ldots C_{n-1})$,
      one of said intermediate washing stations being a latter stage washing station for completely discharging the washing liquid having a concentration of the reacted substance $(C_{n-1})$ from the reaction container into a latter stage reuse container belonging thereto, and feeding pure washing liquid into the reaction container so as to obtain a washing liquid having a concentration of the reacted substance $(C_n)$, and
      a final washing station for discharging a washing liquid having a concentration of the reacted substance $(C_n)$ from the reaction container into a final station reuse container belonging thereto,
   wherein the washing liquid fed into the reaction container at each washing station is fed from the reuse container belonging to a washing station downstream thereof, and the concentration of the reacted substances ($C_1$, $C_2, C_3, C_4, C_5 \ldots C_{n-1}, C_n$) are successively lower.

* * * * *

UNITED STATES PATENT AND TRADEMARK OFFICE
CERTIFICATE OF CORRECTION

PATENT NO.    : 6,500,388 B1
DATED         : December 31, 2002
INVENTOR(S)   : Nagaoka et al.

It is certified that error appears in the above-identified patent and that said Letters Patent is hereby corrected as shown below:

<u>Title page,</u>
Please correct [*] Notice: as follows:

-- [*] Notice: This patent issued on a continued prosecution application filed under 37 CFR 1.53(d), and is subject to the twenty year patent term provisions of 35 U.S.C. 154(a)(2)

Subject to any disclaimer, the term of this patent is extended or adjusted under 35 U.S.C. 154(b) by 0 days --

Signed and Sealed this

Tenth Day of June, 2003

JAMES E. ROGAN
*Director of the United States Patent and Trademark Office*